(12) United States Patent
Santos et al.

US010548841B2

(10) Patent No.: US 10,548,841 B2
(45) Date of Patent: Feb. 4, 2020

(54) LIPOSOME FORMULATIONS

(71) Applicant: OPKO Pharmaceuticals, LLC, Miami, FL (US)

(72) Inventors: Arturo Santos, Zapopan (MX); Phillip Frost, Miami Beach, FL (US)

(73) Assignee: OPKO Pharmaceuticals, LLC, Miami, FL (US)

( * ) Notice: Subject to any disclaimer, the term of this patent is extended or adjusted under 35 U.S.C. 154(b) by 511 days.

(21) Appl. No.: 14/422,587

(22) PCT Filed: Aug. 15, 2013

(86) PCT No.: PCT/US2013/055084
§ 371 (c)(1),
(2) Date: Feb. 19, 2015

(87) PCT Pub. No.: WO2014/031429
PCT Pub. Date: Feb. 27, 2014

(65) Prior Publication Data
US 2015/0224055 A1 Aug. 13, 2015

Related U.S. Application Data

(60) Provisional application No. 61/862,300, filed on Aug. 15, 2013, provisional application No. 61/791,693, filed on Mar. 15, 2013, provisional application No. 61/691,455, filed on Aug. 21, 2012.

(51) Int. Cl.
| | | |
|---|---|---|
| *A61K 9/127* | (2006.01) |
| *C07K 16/22* | (2006.01) |
| *A61K 9/00* | (2006.01) |
| *A61K 31/58* | (2006.01) |
| *A61K 39/395* | (2006.01) |
| *A61K 45/06* | (2006.01) |
| *A61K 39/00* | (2006.01) |

(52) U.S. Cl.
CPC .......... *A61K 9/1271* (2013.01); *A61K 9/0048* (2013.01); *A61K 31/58* (2013.01); *A61K 39/3955* (2013.01); *A61K 45/06* (2013.01); *C07K 16/22* (2013.01); *A61K 2039/505* (2013.01); *A61K 2039/55555* (2013.01)

(58) Field of Classification Search
CPC .............. A61K 9/127; A61K 2039/505; A61K 2039/55555; A61K 31/58; A61K 39/3955; A61K 45/06; A61K 9/0048; A61K 9/1271; A61K 9/0019; A61K 9/08; A61K 39/39558; A61K 39/395; C07K 16/22; C07K 2317/55; A61P 27/02
See application file for complete search history.

(56) References Cited

U.S. PATENT DOCUMENTS

| | | | |
|---|---|---|---|
| 6,565,861 B1 | 5/2003 | Tiffany et al. | |
| 6,610,322 B1 | 8/2003 | Keller et al. | |
| 6,958,160 B1 * | 10/2005 | Keller | A61K 9/1271 264/4.1 |
| 2004/0071761 A1 | 4/2004 | Miller et al. | |
| 2006/0165744 A1 | 7/2006 | Jamil et al. | |
| 2007/0148225 A1 | 6/2007 | Weiner et al. | |
| 2011/0033468 A1 * | 2/2011 | Shih | A61K 9/0019 424/139.1 |
| 2011/0033527 A1 | 2/2011 | Wu et al. | |
| 2011/0040113 A1 | 2/2011 | Wu et al. | |
| 2011/0097340 A1 | 4/2011 | Ramachandra et al. | |
| 2011/0230476 A1 | 9/2011 | Niu et al. | |
| 2012/0009185 A1 * | 1/2012 | Shams | C07K 16/22 424/133.1 |

FOREIGN PATENT DOCUMENTS

| | | | | |
|---|---|---|---|---|
| WO | 2007076274 A2 | 7/2007 | | |
| WO | WO 2010065834 A1 * | 6/2010 | ......... | C12N 15/1136 |

OTHER PUBLICATIONS

Janssen, A., et al., "Peptide-Targeted Peg-Liposomes In Anti-Angiogenic Therapy", International Journal of Pharmaceutics, vol. 254, pp. 55 58, (2003).
Lee, V., et al., "Ocular Drug Bioavaliability from Topically Applied Liposomes", Survey of Ophthalmology, vol. 29, No. 5, pp. 335-348, (1985).
Singh, K, et al., "Liposomal Ophthalmic Drug Delivery System Triamcinolone Acetonide", International Journal of Pharmaceutics, vol. 16, pp. 339-344, (1983).
Moshfeghi, D., et al., "Acute Endophthalmitis Following Intravitreal Triamcinolone Acetonide Injection", American Journal of Ophthomoiogy, vol. 103, pp. 791-796, (2003).
Becerra, E., et al., "Clinical Evidence of intravitreal Triamcinolone Acetonide in the Management of Age-Related Macular Degeneration", Current Drug Targets, vol. 12, No. 2, pp. 149-172, (2011). Abstract.
Suzuki, Y., et al., "Retinoic Acid Controls Blood Vessel Formation by Modulating Endothelial and Mural Cell Interaction Via Suppression of Tie2 Signaling in Vascular Progenitor Cells", Blood, vol. 104, No. 1, pp. 166-169, (2004).
Araujo, J., et al., "Release Profile and Transscleral Permeation of Triarncinolone Acetonide Loaded Nosnostructed Lipid Carriers (TA-NLC): In Vitro and Ex Vivo Studies", Nanomedicine, vol. 8, No, 6, pp. 1034-1041, (2011).

(Continued)

*Primary Examiner* — Snigdha Maewall
(74) *Attorney, Agent, or Firm* — OPKO Pharmaceuticals, LLC; Monte R. Browder

(57) ABSTRACT

The present invention relates to pharmaceutical formulations comprising an anti angiogenic compound such as a monoclonal antibody or fragment thereof selected from, for example, ranibizumab, which is a vascular endothelial growth factor binder which inhibits the action of VEGF, and a delivery agent selected from a pharmaceutically acceptable liposome. The formulations are useful in the treatment of a variety of angiogenic disorders and diseases in animals and people, and, preferably, in ophthalmic disorders selected from age-related macular degeneration, diabetic macular edema and corneal neovascularization.

16 Claims, 7 Drawing Sheets

(56) References Cited

OTHER PUBLICATIONS

Liu, H., et al., "A Lipid Nanoparticle System Improves sIRNA Efficacy in RPE Cells and a Laser-Induced Murine CNV Model", Investigative Ophthalmology & Visual Science, vol. 52, No. 7, pp. 4789-4794, (2011).
Shimazaki, H., et al, "Edaravone-Loaded Liposome Edyedrops Protects Against Light-Induced Retinal Damage in Mice", Investigative Ophthalmology & Visual Science, vol. 52, No. 10, pp. 7289-7297, (2011).
Nishimura, E., "Drug Treatment for Diabetic Retinopathy: Current and Future", Journal of The Showa University Society , vol. 70, No. 1, pp. 45-51, (2010).
Yilmaz, T., et al. "Triamcinolone and Intraocular Sustained-Release Delivery Systems in Diabetic Retinopathy", Current Pharmaceutical Biotechnology, vol. 12, No. 3, pp. 337-346, (2011).
Rui, A., "Retina", Tianjin Science and Technolgy Translation and Publishing Company, pp. 2235-2236, (2011).
Allen, T., et al., "Drug Delivery Systems: Entering the Mainstream", Science, vol. 303, pp. 1818-1822, (2004).
Altamirano-Vallejo, J., et al., "Characterization and Pharmacokinetics of Triamcinolone Acetonide-Loaded Liposomes Topical Formulations for Vitreretinal Drug Delivery", Journal of Ocular Pharmacology and Therapeutics, vol. 34, pp. 416-425, (2018).
Arikan, G., et al., "Immediate intraocular Pressure Rise After intravitreal Injection of Ranibizumab and Two Doses of Triamcinolone Acetonide", International Journal of Ophthalmology, vol. 4, No. 4, pp. 402-405, (2011).
Bangham, A., et al., "Negative Staining of Phospholipids and Their Structural lodification by Surface-Active Agents as Observed in the Electron Microscope", Journal of Molecular Biology, vol. 8, pp. 660-668, (1964).
Bochot, A., et al., "Liposomes for Intrevitreal Drug Delivery: A State of the Art", Journal of Controlled Release, vol. 161, pp. 628-634, (2012).
Campochiaro, P., et al., "Ranibizumah for Macular Edema Due to Retinal Vein Occlusions: Implication of VEGF as a Critical Stimulator", Molecular Therapy, vol. 16, No. 4, pp. 791-799, (2008).
Chan. CK, et al., "Ocular-Hypertensive Response and Corneal Endothelial Changes After Intravitreal Triamcinolone Injections in Chinese Subjects: A 6-Months Follow-Up Study", Eye, vol. 19, pp. 625-630, (2005).
Chu, YK., et al., "Objective Evaluationof Cataract Progression Associated with a High Dose Intravitreal Triamcinolone Injection", Eye, vol. 22, pp. 895-899, (2008).
Cugati, S., et al., "Ten-Year Incidence of Retinal Vein Occlusion in an Older Population", The Archives of Ophthalmology, vol. 124, pp. 726-732, (2006).
Ebrahem, Q., et al., "Triamcinolone Acetonide Inhibits IL-6-and VEGF-Induced Angiogenesis Downstream of the IL-6 and VEGF Receptors", Investigative Ophthalmology & Vision Science, vol. 47, No. 11, pp. 4935-4941, (2006).
Feigenbaum, A., et al., "Intravitreal Injection of Penicillin in a Case of Incipient Ahcess of the Vitreous Following Extracapsular Cataract Extraction; Perfect Cure", Ophthalmologica, vol. 110, pp. 300-305, (1945).
Gaudana, R., et al., "Ocular Drug Delivery", The AAPS Journal, vol. 12, No. 3, pp. 348-360, (2010).
Gaudana, R., et al., "Recent Perspective in Ocular Drug Delivery", Pharmaceutical Research , vol. 26, No. 5, pp. 1197-1216, (2009).
Habot-Wilner, Z., et al., "Intravitreal Triamcinolone Acetonide as Adjunctive Treatment with Systemic Therapy for Uveitic Macular Edema", European Journal of Ophthalmology, vol. 21, Suppl. 6 pp. S56-S61, (2011).
Haller J. et al., "Randomized, Sham-Controlled Trial of Dexamethasone Intravitreal Implant in Patients with Macular Edema Due to Retinal Vein Occlusion", Ophthalmology, vol. 117, pp. 1134-1146, (2010).
Jonas, J., et al., "Branch Retinal Vein Occlusion Treated by Intravitreal Triamcinolone Acetonide", Eye, vol. 19, pp. 65-71, (2005).

Kim, J., et al., "A Prospective, Randomized, Dose-Escalation Intravitreal Steroid Injection Study for Refractory Diabetic Macular Edema" Retina, vol. 28, pp. 735-740, (2008).
Kim, S., et al., "Transport Barriers in Transscleral Drug Delivery for Retinal Diseases", Ophthalmic Research, vol. 39, pp. 244-254, (2007).
Klibanov A., et al., "Amphipathic Polyethylenegiycols Effectively Prolong the Circulation Time of Liposomes", FE, vol. 268, No. 1, pp. 235-237, (1990).
Kwon, S., et al., "Comparison of Natural Course, Intravitreal Triamcinolone, and Intravitreal Bevacizumab for Treatment of Macular Edema Secondary to Branch Retinal Vein Occlusion", Journal of Ocular Pharmacology and Therapeutics, vol. 29, No. 1, pp. 5-9, (2013).
Lam, D., et al., "Intravitreal Triamcinolone for Diabetic Macular Oedema in Chinese Patients: Six-Month Prospective Longitudinal Pilot Study", Clinical Exp Ophthalmology, vol. 32, pp. 562-572, (2004).
Lee, H., et al., "Intravitreal Triamcinolone as Primary Treatment of Cystoid Macular Edema Secondary to Branch Retinal Vein Occlusion", Retina, vol. 25, pp. 551-555, (2005).
Lee, S. et al., "Evaluation of Clearance Mechanisms with Transscleral Drug Delivery", Investigative Ophthalmology & Visual Science, vol. 52, No. 10, pp. 5205-5212, (2010).
Lopez-Berestein, G., et al., "Effects of Sterols on the Therapeutic Efficacy of Liposornal Amphotericin B in Murine Candidiasis", Cancer Drug Delivery, vol. 1, No. 1, pp. 37-42, (1983).
Mansoor, S.,et al., "Intraocular Sustained-Release Delivery Systems for Triamcinolone Acetonide", Pharmaceutical Research, vol. 26, No. 4, pp. 770-784, (2009).
McAllister I., et al., "Effect of Triamcinolone Acetonide on Vascular Endothelia Growth Factor and Occludin Levels in Branch Retinal Vein", The American Journal of Ophthalmology , vol. 147, pp. 838-846, (2009).
Noma, H., et al., "Pathogenesis of Macular Edema with Branch Retinal Vein Occlusion and Intraocular Levels of Vascular Endothelial Growth Factor and Interleukin-6", American Journal of Opthalrnology, vol. 140, pp. 256-261, (2005).
Noma, H., et al., "Intravitrael Levels of Vascular Endothelial Growth Factor and Interteukin-6 are Correlated with Macular Edema in Branch Retinal Vein Occlusion" Graefe's Archive for Clinical and Experimental Ophthalmology, vol. 244, pp. 309-315, (2006).
Oku, N., "Anticancer Therapy Using Glucuronate Modified Long-Circulating Liposomes", Advanced Drug Delivery Reviews, vol. 40, pp. 63-73, (1999).
Oku, N., "Selective Release of Non-Electrolytes from Liposomes Upon Perturbatiopn of Bilayers by Temperature Change of Polyene Antibiotics", Biochimica et Biophysica Acta, vol. 595, pp. 277-290, (1980).
Park, S., et al., "Aqueous Vascular Endothelial Growth Factor Levels Are Associated with Serous Macular Detachment Secondary to Branch Retinal Vein Occlusion" Retina, vol. 30, pp. 281-286, (2010).
Rogers, S., et al., "The Prevalence of Retinal Vein Occlusion: Pooled Data From Population Studies from the United States, Europe, Asia, and Australia" Ophthalmology, vol. 117, No. 2, pp. 313-319, (2010).
Scott, I. et al., "A Randomized Trial Comparing the Efficacy and Safety of Intravitreal Triamcinolone with Standard Care to Treat Vision Loss Associated with Macular Edema Secondary to Branch Retinal Vein Occlusion: The Standard Care vs. Corticosteroid for Retinal Vein Occlusion (SCORE) Study Report 6", The Archives of Ophthalmology, vol. 127, pp. 1115-1128, (2009).
Shubber, S., et al., "Mechanism of Mucosal Permeability Enhancement of CriticalSorb (R) (Solutol(R) HS15) Investigated in Vitro in Cell Cultures", Pharmaceutical Research, vol. 32, pp. 516-527, (2015).
Smithen, L., "Intravitreal Triamcinolone Acetonide and Intraocular Pressure", The American Journal of Ophthalmology, vol. 138, 740-743, (2004).
Van Rooijen, N., et al., "Liposomes in Immunology: Multilamellar Phosphatidylcholine Liposomes as a Simple, Biodegradable and

(56) References Cited

OTHER PUBLICATIONS

Harmless Adjuvant Without Any Immunologertic acitivity of its Own", Immunological Communications, vol. 9, No. 3, pp. 243-256, (1980).

Veritti D., et al., "Drug Safety Evaluation of Intravitreal Triamcinolone Acetonide", Expert Opinion Drug Safety, vol. 11, pp. 331-340, (2012).

Wingate, R., "Intravitreal Triamcinolone and Elevated intraocular Pressure", Ophthalmology, vol. 27, pp. 431-432, (1999).

Yalcinbayir, O., et al., "Intravitreal Versus Sub-Tenon Posterior Triamcinolone Injection in Bilateral Diffuse Diabetic Macular Edema", Oplithalmologica, vol. 225, pp. 222-227, (2011).

Young, S., et al., "Safety and Efficacy of Intravitreal Triamcinolone for Cystoid Macular Oedema in Uveitis", Clinical Experimental and Ophthalmology, vol. 29, pp. 2-6, (2001).

Zhang X., et al., "Glucocorticoids: Structure, Signaling and Molecular Mechanisms in the Treatment of Diabetic Retinopathy and Diabetic Macular Edema", Current Molecular Medicine, vol. 14, No. 3, pp. 376-384, (2014).

Gonzalez-De La Rosa, A., et al., "Novel Triamcinolone Acetonide-Loaded Liposomes Topical Formulation for the Treatment of Cystoid Macular Edema After Cataract Surgery: A Pilot Study", Journal of Ocular Pharmacology and Therapeutics, vol. 35, No. 2, pp. 106-115, (2019).

Lee, V., et al., "Ocular Drug Bioavailability From Topically Applied Liposomes", Survey of Ophthalmology, vol. 29, No. 5, pp. 335-349, (1985).

Singh, K., et al., "Liposomal Ophthalmic Drug Delivery system I. Triamcinolone Acetonide", International Journal of Pharmaceutics, vol. 16, No. 3, pp. 339-344. (1983). Abstract.

\* cited by examiner

Phase contrast optical microscopy of QuSomes: multilamellar vesicles (left) and large unilamellar vesicles (right), 10 minutes after addition of water.

Result: Central Foveal Thickness-Study Eyes Over Time

Results: Central Foveal Thickness-Contra-lateral eyes

Results: BCVA-Study Eyes

Results: BCVA Contra-lateral eyes

LIPOSOME FORMULATIONS

CROSS-REFERENCE TO RELATED APPLICATIONS

The present application claims priority to U.S. Provisional Patent Applications 61/691,455, 61/791,693, and 61/862,300, filed Aug. 21, 2012; Mar. 15, 2013; and Aug. 5, 2013, respectively, all of which are incorporated by reference herein in their entirety.

FIELD OF THE INVENTION

The present invention relates to pharmaceutical formulations comprising an ophthalmic medication typically applied by intravitreal injection to the eye and a liposomal deliver agent that permits topical application to the eye of said intravitreal medication. The present invention also relates to an anti-angiogenic compound such as a monoclonal antibody or fragment thereof selected from, for example, ranibizumab, which is a vascular endothelial growth factor binder which inhibits the action of VEGF, and/or a multi-kinase VEGFR and PDGFR inhibitor, for example, sunitinib, and a delivery agent selected from a pharmaceutically acceptable liposome. The formulations are useful in the treatment of a variety of angiogenic disorders and diseases in animals and people, and, preferably, in ophthalmic disorders selected from age-related macular degeneration, diabetic macular edema and corneal neovascularization.

BACKGROUND OF THE INVENTION

Ophthalmic disease treatment typically requires either topical administration or intravitreal injection of the particular drug to the eye depending upon the particular disease or condition and the effectiveness of the route of administration with respect to the particular drug and disease. In certain diseases or conditions of the eye effective treatment can only be achieved if the drug is administered by intravitreal injection. There are a litany of diseases and conditions of the eye that are effectively treated by intravitreal injection. At the same time, these injections can cause and/or are associated with serious side effects including eye infections (endophthalmitis), eye inflammation, retinal detachments and increases in eye pressure. Because of these side effects or risks topical treatment of the eye has been both the preferred route of administration of drugs to treat eye conditions and the Holy Grail because in almost all cases, topical administration of the drug does not effectively treat certain eve conditions, especially those conditions that occur in the back of the eye. Thus there is a need to develop formulations that effectively treat said conditions and that eliminate the need to have intravitreal injections. The present inventors believe they have found such a vehicle, U.S. Pat. No. 6,884,879 discloses various anti-VEGF antibodies. This patent specifically describes and claims the monoclonal antibody ranibizumab which is approved and marketed under the brand name LUCENTIS®. The antibodies disclosed therein are described as being capable of preventing, reversing and/or alleviating the symptoms of various diseases and are described as having the ability to inhibit VEGF-induced proliferation of endothelial cells and the ability to inhibit VEGF-induced angiogenesis. LUCENTIS® is approved for neovascular (wet) age-related macular degeneration (AMD) at a dosage strength of 0.5 mg (0.05 mL) by intravitreal injection one a month and, though less effective, the approved treatment may be administered to an injection every three months after an initial regimen of once a month for at least four months. LUCENTIS® is also approved in the United States for macular edema following retinal vein occlusion (RVO) using 0.5 mg (0.05 mL) on a once-a-month intravitreal regimen. In addition, LUCENTIS® is approved in Europe and in the United States for diabetic macular edema in the injectable formulation.

Sunitinib (SU-11248, Sutent), was approved January 2006 by FDA as a monotheraphy for the treatment of metastatic renal cell cancer and gastrointestinal stromal tumors. Sunitinib inhibits at least eight receptor protein-tyrosine kinases including vascular endothelial growth factor receptors 1-3 (VEGFR1-VEGFR3), platelet-derived growth factor receptors (PDGFRα and PDGFRβ). This compound inhibits angiogenesis by diminishing signaling through VEGFR1, VEGFR2, and PDGFRβ. PDGFRβ is found in pericytes that surround capillary endothelial cells [1](Roskosiki 2007, PDF document attached). There is evidence that the combined use of an anti-PDGF is superior to ranibizumab monotherapy in the treatment of some VEGF related diseases.

There are multiple side effects or potential side effects including patient discomfort associated with the intravitreal injection of anti-VEGF antibodies and other ophthalmic drugs. The intravitreal injection procedure requires a dedicated clean room with ordinary aseptic rules; resuscitation facilities must be immediately available. Complications of this procedure include infectious endophthalmitis; retinal detachment and traumatic cataract. Other possible complications of intravitreal injection include intraocular pressure changes, especially intraocular pressure elevations. Injection related intraocular pressure elevations which can occur immediately after injection of any kind of medication and drug specific-related intraocular pressure changes which may be detected days or even months after the injection. See Semin. Ophthamol. 2009 March-April; 24(2):100-5.

There is an urgent unmet medical need for new topical treatment regimens of such anti-VEGF antibodies and other effective ophthalmic drugs such as antimicrobials, antivirals, corticosteroids and anti-vascular endothelial growth factor agents which are the main classes of drugs that are administered through intravitreal injections. The present invention comprises a combination of said Liposomes and any of said drugs within said drug classes in a topical formulation. While U.S. Pat. No. 6,884,879 generally discloses various possible delivery methods or reagents including liposomes and various mutes of administration including topical administration of such VEGF monoclonal antibodies, the only approved form of ranibizumab is the intravitreal form in a liquid formulation. There is a need for topical ranibizumab formulations that are effective in treating people having VEGF related disorders including ophthalmic disorders.

The inventors have met this unmet need and have surprisingly found that certain liposomal formulations comprising such VEGF monoclonal antibodies and certain liposomes provide effective relief in patients having diabetic macular edema. The formulations can be effectively administered topically to the affected eye and are more effective than topical application of the intravitreal formulation. U.S. Pat. No. 6,958,160 discloses and claims self-forming, thermodynamically stable liposomes. U.S. Pat. Pub. No. 2010/0076209, hereby incorporated by reference, discloses PEG-lipid conjugates for liposomes and drug delivery. Various lipid based products including such self-forming thermodynamically stable liposomes marketed under the brand name Qsomes™ (hereinafter Qsome) are sold by Biozone Laboratories for multiple therapeutic uses and via various routes of administration including by topical administration to the skin. The inventors have discovered that a pharmaceutical composition comprising ranibizumab and such self forming, thermodynamically stable liposomes and/or PEG-lipid conjugates can be delivered topically to the eye of a patient in need of treatment of VEGF related ophthalmic diseases and conditions. The present invention further comprises a topical formulation comprising a Qsome as recited herein (self-forming thermodynamically stable liposome) and a drug wherein the formulation is suitable for the treatment of a posterior segment ophthalmic disease and/or a disease that is a combination anterior segment/posterior segment disease. The claimed formulations are suitable for topical administration and are particularly useful in treating ophthalmic diseases and conditions that are typically treated via a periocular route or via intravitreal administration (intraocular delivery). Periocular administration includes subconjunctival, subtenon, retrobulbar and peribulbar administration. There are some drugs that have been disclosed as being able to be delivered to the posterior segment by topical administration-these include ESBA105, an anti-INF-alpha single chain antibody; dexamethasone; nepafenac; memantine HCl; dorzolamide: brimonidine and betaxolol. It is believed that topical administration of these drugs in a Qsome formulation will result in more effective topical delivery and more effective posterior segment delivery. Preferably, however, the claimed invention comprises a topical formulation including a Qsome liposome as described herein and drugs which heretofore have not been effectively delivered through topical administration.

Drugs typically given by intravitreal injection include antimicrobials, antivirals, corticosteroids and anti-vascular endothelial growth factor agents. The present invention comprises a liposomal formulation comprising a self-forming thermodynamically stable liposome and an active pharmaceutical agent selected from any one of or a combination of an antimicrobial, antiviral, corticosteroid and anti-vascular endothelial growth factor agent wherein said formulation is suitable for topical delivery to the eye of a patient to treat an ophthalmic disease or condition. Diclofenac, gatifloxacin, sparfloxcain lactate, GCV, demeclocycline, flubiprofen, doxorubicin, celecoxib, budesonide and cisplatin have been formulated in colloidal dosage forms for transcorneal or transcleral delivery. Cationic liposomes containing penicillin G, tropicamide and acetazolamide have been used to provide maximum drug, transport across the cornea relative to anionic and neutral liposomes. See Schaeffer et al. Liposomes in topical drug deliver. Invest. Ophthalmol. Vis Sci. 198:222(2):220-7; Nagarsenker et al. Preparation and evaluation of liposomal formulations of tropicamide for ocular delivery. Int J Pharma. 1999:190(1)163-71 and Hathout et al. Liposome as an ocular delivery system for acetazolamide: in vitro and in vivo studies. AAPS Pharma Sci Tech. 2007; 8(1):1.

Diabetic retinopathy (DR) is the most common microvascular complication of diabetes [2](Fong, 2004) and is the leading cause of new cases of vision loss among working-aged adults. Diabetic macular edema (DME) is the most common cause of vision loss in patients having DR. The prevalence of DME is 3% recent diagnosis with about 75,000 new cases of DME each year (USA). The number of worldwide patients having diabetes is a staggering 285 million. DME results from a series of biochemical and cellular changes that ultimately cause progressive leakage and exudation, leading to thickening of the retina and hard exudates within 1 disc diameter of the center of the macula. DME is one of the most common causes of impaired vision in patients with diabetes [3](Bhagat, 2009). Approximately 50% of patients experience a loss of ≥2 lines of BCVA after two years of follow-up [4](Meyer, 2007).

In DME, damaged blood vessels leak fluid into the central portion of the retina (macula) which leads to swelling. The macula is involved with sharp central vision. The fovea is at the center of the macula. DME can occur in patients having type 1 or type 2 diabetes. Approximately 26 million people in the United States have diabetes and 1.9 million new cases are diagnosed in people aged 20 and older each year. Up to 75,000 new cases of DME are estimated to develop each year. DME is a leading cause of blindness among the working-age population in most developed countries. First line therapy for DME is laser surgery which seals the leaky blood vessels to diminish the leakage of fluid and reduce the amount of fluid in the retina. There is thus a significant need to create new formulations that provide therapeutic relief to these patients.

SUMMARY OF THE INVENTION

The present invention is a pharmaceutical formulation comprising an anti-angiogenic compound or other ophthalmic active ingredient and a liposome. The preferred anti-angiogenic compounds are anti-VEGF antibodies. The pharmaceutical formulation is preferably administered as a topical formulation to the eye of a patient in need of treatment thereof. The pharmaceutical formulation is useful in the treatment of VEGF related ophthalmic disorders including, for example, age related macular degeneration and diabetic macular edema. The present invention is also directed to formulations suitable for topical administration and which are effective in treating corneal neovascular disease.

The preferred anti-VEGF antibody is selected from ranibizumab (LUCENTIS®) and may be prepared as described in U.S. Pat. No. 6,884,879 which is hereby incorporated-by-reference. This product is sold as a prescription intravitreal liquid formulation. Ranibizumab is a recombinant humanized IgG1 kappa isotype monoclonal antibody fragment. This antibody binds to and inhibits VEGF-A and has a molecular weight of approximately 48 kilodaltons. The product is produced in an *E. coli* expression system in a nutrient medium that contains tetracycline. The prescription product is supplied in a single use glass vial containing 0.05 mL of a 10 mg/mL of ranibizumab. Other anti-VEGF antibodies such as bevacizumab may also be used to treat certain diseases and conditions such as corneal neovascular disease. The topical liposomal formulation disclosed herein facilitates penetration of whole antibodies such as bevacizumab into eyes having abnormal neovascularature.

The liposomes useful in the present invention preferably comprise those liposomes that are described in U.S. Pat. No. 6,958,160 which is hereby incorporated by reference in its entirety. As described therein, liposomes are self-closed colloidal particles wherein membranes composed of one or more lipid bilayers encapsulate a fraction of the aqueous solution in which they are suspended. As also recited in the '160 patent, not all liposomes are the same and, in fact, liposomes can have problems including colloidal instability and manufacturing issues due to extreme conditions such as elevated pressures and temperatures as well as high shear conditions—all of which can degrade the lipid components. Other issues associated with liposomes in general can include heterogeneous distributions of sizes and numbers of bilayers which can cause or acerbate scale-up issues. In addition, sterilization conditions can also create issues with liposomes. Liposomes also may have colloidal instability due to aggregation while in suspension. This leads to fusion issues and the solution to this problem is typically lyophilization which is a costly extra step. The liposomes disclosed in the '160 patent have overcome these problems and it has been surprisingly found that these particular liposomes are effective when combined with anti-VEGF antibodies such as ranibizumab.

In particular, a formulation comprising self-forming, thermodynamically stable liposomes and an anti-VEGF antibody is particular suitable for topical application in the treatment of VEGF related ophthalmic diseases and conditions.

The liposomes useful in the present formulation comprise diacylglycerol-PEG compounds. The melting point of these compounds is below about 40° C. and the acyl chains are greater than or equal to about 14 carbons in length. These compounds are prepared as recited in the '160 patent. The preferred lipid PEG conjugate is PEG-12-GDM (Polyethylene glycol 12-Glycerol Dimyristate). PEG stabilizes the liposomes by creating a steric barrier at the outer surface of the liposomes, the PEG chain has a molecular weight between about 300 Daltons and 5000 Daltons. Liposome preparation entails merely mixing the lipid with an aqueous solution. These kinds of liposomes exist in the lowest energy state that the lipid can exist in while in aqueous solution, reproducibility of liposome formation is no problem.

A defined lipid, lipid mixture, or lipids/compound mixture will form similar liposomes every time when mixed with the same aqueous solution. Above critical concentrations (around 20% weight to volume) non-liposomal structures will begin to form in aqueous solution. These liposomes exist in their lowest energy state and are thermodynamically stable, self-forming liposomes. PEG-12 GDM forms very small vesicles so they can be sterile filtered. Kinetic energy, such as shaking or vortexing, may be provided to the lipid solution and the aqueous solution. The present formulation may also use other lipid-PEG conjugates as generally or specifically described in the U.S. Pat. No. 6,958,160. In addition, other lipid PEG self-forming, thermodynamically stable conjugates may also be used including those compounds described in US Pat Pub. No, 2010/0076209. Table 1 below describes certain PEG-12 GDM characteristics.

TABLE 1

PEG-12 GDM CHARACTERISTICS:

| LIPID | MELTING POINT (° C.) | Pa | Pv | SPONTANEOUS LIPOSOMES AT 20° C. | SPONTANEOUS LIPOSOMES AT 37° C. |
|---|---|---|---|---|---|
| PEG-12 GDM | Fluid @ 25 | 0.829 | 0.869 | YES | YES |

MOLECULAR WEIGHT: 1068 g/mol
OPTIMUM pH: 5-7
SOLUBILITY: Soluble in organic solvents.

In the ranibizumab topical formulation of the present invention. 1% weight volume of PEG-12 GDM based upon the final volume of solution was used and having a pH of the topical solution of 5.5 and in the appropriate range of working with the liposome.

In addition to the anti-angiogenic compound (e.g. the anti-VEGF antibody) and the thermodynamically stable, self-forming liposome, the formulation may further comprise additional pharmaceutically acceptable excipients. The preferred excipients are selected from the group consisting of excipients suitable for topical administration to the eye. These include surfactants, buffer reagents, pH modifiers, salts and other such ingredients.

The formulations are useful in treating VEGF related diseases and conditions and/or other angiogenic conditions. The present invention thus includes use of such formulations to treat age related macular degeneration, diabetic retinal diseases including diabetic macular edema and corneal neovascularization. In a preferred embodiment, the invention comprises a topical formulation and encompasses a method of treating such VEGF related diseases and conditions by topically administering such formulations to the eye of a patient in need of treatment thereof.

BRIEF DESCRIPTION OF THE DRAWINGS

The invention will he described in the following figures.

FIG. 1 shows improvement in CFT occurring again from the 12 week to 14 week period.

FIG. 1 shows improvement in VA occurring again from the 12 week to 14 week period.

DETAILED DESCRIPTION

Figure 1:
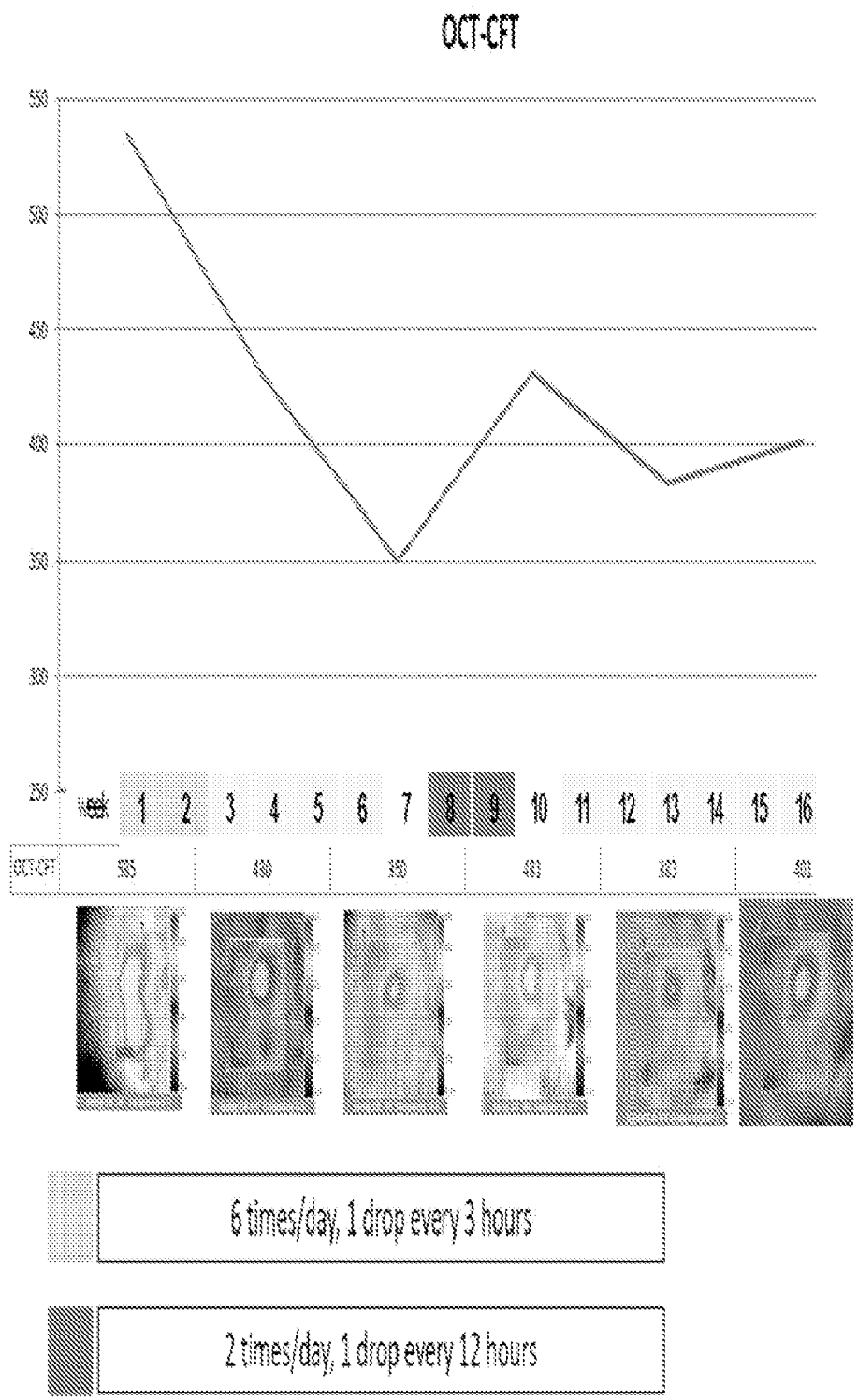
FIG. 1 shows data from a single patient treated with a liposomal ranibizumab formulation having improved central foveal thickness measurements using optical coherence topography (OCT-CFT) over an eight week period after being dosed six drops per day for two weeks. At week eight the patient showed an increase in CFT and treatment was reinitiated at 10 weeks at a daily dose of 2 drops per day.

The present invention relates to pharmaceutical formulations and uses thereof wherein the preferred formulation comprises an anti-VEGF antibody and a self-forming, thermodynamically stable liposome. The present invention also relates to a topical formulation comprising an anti-VEGF antibody and a self-forming, thermodynamically stable liposome. The invention further comprises a method of treating a VEGF related disease or condition comprising administration of a formulation comprising an anti-VEGF antibody and a self-forming, thermodynamically stable liposome to a patient in need of treatment thereof. In a preferred embodiment the VEGF related disease or condition is selected from a diabetic retinopathy (DR).

While liposomes "in general" have been described in connection with the delivery of various active ingredients, the art does not disclose or teach the combination of self-forming, thermodynamically stable liposomes in combination with anti-VEGF antibodies. The liposomes of the formulation are particularly suitable for delivery of anti-VEGF antibodies to a patient in need of treatment of a VEGF-related disease or condition and, in particular, to ophthalmic diseases or conditions. The liposomal formulations of the present invention are particularly suited for topical administration to the eye of a patient in need of treatment of, for example, diabetic macular edema or age-related macular degeneration or corneal neovascularization. The liposomes of the present invention have desired fundamental properties that make them especially suitable for these topical formulations. The liposome suspensions are thermodynamically stable at the temperature of formulation. The compositions of the lipids that make up the liposome have several fundamental properties. The lipids have packing parameters that allow the formation of liposomes. The lipids include, as part of the head group, a polyethyleneglycol (PEG) or polymer of similar properties that sterically stabilizes the liposomes in suspension. In addition, the liposomes have a melting temperature that allows them to be in liquid form when mixed with water or an aqueous solution.

As described in the U.S. Pat. No. 6,610,322, little or no energy need be added when forming the liposomal suspensions in aqueous solution. In the present invention, the preferred method involves forming the liposomal suspension in the presence of an aqueous solution containing the active ingredient-the anti-VEGF antibody. Self-assembly thus preferably occurs with the active ingredient rather than before the active ingredient is added to the suspension. The lipid molecules disperse and self assemble into the natural low energy state. The liposomes form large or small unilamellar vesicles (SUVs) or multilamellar vesicles (MLVs) (see FIG. 3) and as described in the Biozone Laboratories website for Qusomes™.

The PEG chain preferably has a molecular weight of between about 300 Daltons and 5000 Daltons. Examples of suitable lipids include PEG-12 GDO (glycerol dioleate) and PEG-12 GDM (glycerol dimyristate). PEG-12 GDM is fluid at 25° C. and has packing parameters $P_a$ and $P_v$ of 0.853 and 0.889 respectively. Each of these lipids form spontaneous liposomes at 20° C., 37° C. and 60° C. The Pa may range between 0.84 and 0.88 and the Pv between about 0.88 and 0.93. Preferably, the suitable compounds form liposomes instead of, for example, micelles. In addition, the lipid composition should have a phase transition temperature of between about 0° C. and 100° C.—the lipid composition has a melting temperature which allows the composition to be in liquid form when mixed with an aqueous solution. Also, the bending elastic modulus of the composition should be such that the lipid composition can form liposomes in an aqueous environment without the need for any or any significant energy input. Kinetic energy may be applied to the solution. The preferred bending elastic modulus is between about 0 kt and 15 kt. The bending elastic modulus is largely determined by the backbone and glycerol is a preferred backbone of the present invention although any equivalent backbone in terms of bending elastic modulus and suitable functionality may also be used. The relative percentage by weight of the lipid in the final solution may range from greater than 0 to about 20 wt percent (w/w). The range may be between about 1% and 15 wt % or between about 1% and 10% or between about 1% and 5% wt/wt or between greater than 0% and 4% wt/wt.

Mixtures of other molecules and lipids having PEG chains longer than 12 may also be used in the present invention provided they form liposomes. For example, a mixture of PEG-45 GUS (glycerol distearate) and cholesterol forms liposomes. As described in the '322 patent, one of ordinary skill in the art can vary the variables including PEG chain length and components to prepare a thermodynamically stable, free forming liposome and such are included within the scope of the present invention and when combined with an anti-VEGF antibody. The amount of cholesterol when added to the lipid before liposomal formation is up to about 10% w/w.

In addition to the lipids described in the '322 patent, other lipids may also be utilized in the present invention. U.S. Pat. Pub. No. 2010/0076209 describes certain PEG-LIPID conjugates that form liposomes suitable for drug delivery of specifically described active ingredients. There is no teaching of or reference to the delivery of anti-VEGF antibodies in the reference. In particular, diacylglycerol-polyethylene glycol compound as described in the '209 publication may be utilized in combination with anti-VEGF antibodies in the formulations of the present invention. The general structure of the lipid compounds is shown in the '209 publication and includes compounds having the formula (R2)(R1)Glycerol-X-PEG-R1 and/or R1-PEG-X-Glycerol (R2)(R1) wherein R1 is preferably either —OH or —OCH3; R2 and R3 are fatty acids including, and not limited to laurate, oleate, myristate, palmitate, stearate and linoleate; and X represents a single linker or replicate linkers or combination of two or more linkers in between the lipid and PEG. R2 and R3 may be the same or different. If R2 is at the C1 position of glycerol, R3 can be located at either C2 or C3. The general structure includes all racemers and structural isomers and/or functional equivalents thereof.

R1 may also be selected from, for example, —NH2, —COOH, —OCH2CH3, —OCH2CH2CH3, —OCH2CH2OH, —COCH═CH2, —OCH2CH2NH2, —OSO2CH3, —OCH2C6H6, —OCH2COCH2CH2COONC4H4O2, —CH2CH2═CH2 and —OC6H6. Also R1 may be a functional group that helps link or links therapeutic or targeting, agents to the surface of a liposome. These may include amino alkyl esters, maleimide, diglycidyl ether, maleinimido propioinate, methyl carbamate, tosyhydrazone salts, azide, propargyl-amine, propargyl alcohol, NHS esters, hydrazide, succinimidyl ester, succinimidyl tartrate, succinimidyl succinate, and toluesulfonate salts. The present invention includes liposomal formulations having anti-VEGF antibodies within the liposomal composition and may further include any other therapeutic compound including the anti-VEGF antibodies covalently bound or linked to the liposome via the R1 functional group. In such instance, the invention would include or be a combination formulation or a formulation having both a non-covalently bound active ingredient and a covalently bound active ingredient wherein said active may be the same or different.

The linkers useful or suitable in this type of liposomal formulation include those described in the '209 publication and which is hereby incorporated by reference. Table 1 therein describes or lists such suitable linkers and which include amino, succinylamino acetamido, 2-aminopentanamido, 2(2')-R'-aminoacetyl etc. In each case, the lipids form spontaneous liposomes at 20 and 37° C. as shown in Table 4 of the '209 publication. The present invention thus includes those lipids described as PEG-12-N1 -GDO; PEG-23-N2-GDO; PEG-18-N3-GDO; PEG-23-N4-GDO; PEG-8-S1-GDO; PEG-18-S2-GDO; PEG-12-S3-GDO; PEG-18-Ac1-GDO; PEG-12-Ac2-GDO; PEG-12-N1-GDM; PEG-12-N1-GDLO; PEG-12-S3-GDM; PeG-12-S3-GDLO; PEG-12-Ac2-GDM; PEG-12-Ac2-GDLO; PEG-23-N1-GDL; PEG-12kN1-GDP; PEG-23-Ac2-GDL and PEG-12-

Ac2-GDP. GDLO means glycerol dilinoleate and GDP means glycerol dipalmitate. Each of the compounds are fluid at 25° C. and have packing parameters Pa ranging from 0.830 to 0.869 and Pv ranging from 0.872 to 0.924.

The present invention further includes known lipids that meet the physical requirements recited herein and which, for example, are liquid at 25° C. and are self-forming at both 20° C. and 37° C. and have functionally equivalent or equivalent packing parameters and form thermodynamically stable liposomes with little or no energy input when combined, with an aqueous solution.

The anti-VEGF antibodies useful in the present formulation include any known anti-VEGF antibody. These antibodies include whole antibodies or antibody fragments provided they have the requisite anti-VEGF biological properties. In a preferred embodiment, the antibody is an antibody fragment having the requisite anti-VEGF biological and pharmacological properties. U.S. Pat. No. 6,884,879 discloses anti-VEGF antibodies useful in the present invention. Such antibodies include humanized anti-VEGF antibodies and anti-VEGF antibody variants with properties that include strong binding affinity for VEGF; the ability to inhibit VEGF promoted proliferation of endothelial cells and the ability to inhibit VEGF induced angiogenesis. The preferred binding affinity (Kd) is no more than about $5 \times 10^{-9}$ M and with an ED50 value of no more than about 5 nM for inhibiting VEGF-induced proliferation of endothelial cells in vitro. The antibodies include those that inhibit at least about 50% tumor growth in an A673 in vivo tumor model at an antibody dose of 5 mgs/kg. The most preferred antibody is sold under the brand name LUCENTIS® (ranibizumab) and is approved for the treatment of age-related macular degeneration and various forms of macular edema as an intravitreal formulation. The term "anti-VEGF antibody" includes whole antibodies as well as antibody fragments. The range of diseases that can be treated with anti-VEGF antibodies includes those diseases or conditions that are associated with angiogenesis or pathological angiogenesis conditions. These include cancer as well as intraocular neovascular syndromes such as proliferative retinopathies or age-related macular degeneration (AMD), rheumatoid arthritis and psoriasis. While the preferred route of administration is topical treatment to the eye and the preferred disease modality is diabetic macular edema, the formulation recited herein may also be useful in other delivery modes (i.e., injectable intravenous infusion) and in the treatment of the litany of VEGF related diseases and conditions.

The anti-VEGF antibodies include those produced from an isolated nucleic acid encoding a humanized variant of a parent anti-VEGF antibody which parent antibody comprises non-human variable domains, wherein said humanized variant binds human VEGF and has those heavy chain Complementary Determining Region amino acid sequences as described and claimed in the U.S. Pat. No. 6,884,879 which is hereby incorporated by reference. The anti-VEGF antibodies include those that can be produced using vectors having nucleic acid encoding such CDR amino acid sequences and isolated host cells containing such vectors. The host cells can be cultured to produce such sequences and the humanized anti-VEGF antibodies may be recovered from such host cell cultures. The isolated nucleic acid recited above may further encode for a humanized variant having a light chain Complementary Determining Region (CDR) with those sequences as recited in the '879 patent. Such humanized variant may comprise a heavy chain variable domain having sequence shown as SEQ ID NO: 7 and a light chain variable domain having sequence shown as SEQ ID NO: 8 in the '879 patent. Such humanized variant may also comprise a heavy chain variable domain sequence of SEQ ID NO: 116 and a light chain variable domain sequence of SEQ ID NO: 115 as shown in the '879 patent.

U.S. Pat. No. 7,060,269 is also incorporated by reference herein. This patent claims and discloses ranibizumab. Claim 1 of the '269 patent claims a method for inhibiting VEGF-induces angiogenesis in a subject, comprising administering to said subject an effective amount of a humanized anti-VEGF antibody which binds human VEGF with a Kd value of no more than about $1 \times 10^{-8}$, said humanized anti-VEGF antibody comprising a heavy chain variable domain sequence of SEQ ID NO: 116 and a light chain variable domain sequence of SEQ ID NO: 115. Ranibizumab is a recombinant humanized IgG1 kappa isotype monoclonal antibody fragment designed for intraocular use. This monoclonal antibody binds to and inhibits human vascular endothelial growth factor A (VEGF-A). Ranibizumab has a molecular weight of about 48,000 daltons and is produced in an E. coli expression system in a nutrient medium containing tetracycline. This product is commercially available under the tradename LUCENTIS® and is supplied as a preservative free, sterile solution in a single use glass vial that can deliver 0.05 mL of 10 mg/mL ranibizumab aqueous solution with 10 mM histidine HCl, 10% alpha, alpha trehalose dehydrate, 0.01% polysorbate 20, and at a pH of 5.5.

Ranibizumab is described in a scientific journal published in 1999 in the Journal of Molecular Biology (JMB) by Chen et al. entitled "Selection and Analysis of an Optimized Anti-VEGF Antibody: Crystal Structure of an Affinity-matured Fab in complex with Antigen" [5](Chen et al. JMB, 293:865-881 (1999). The heavy chain and light chain sequences of ranibizumab are designated as YO317 in this article and are shown in FIG. 1 therein. In addition to this description, the article also provides data regarding binding affinity of this antibody fragment to VEGF (Table 6 on page 870 therein). Ranibizumab is known to bind to and inhibit the biological activity of VEGF-A which causes neovascularization and leakage in ocular angiogenesis models. Ranibizumab binds to and inhibits VEGF-A and prevents VEGF-A from interacting with the VEGF receptors on the surface of endothelial cells and thus reduces new blood vessel formation (angiogenesis); vascular leakage and endothelial cell proliferation. Administration of a pharmaceutically effective amount of ranibizumab inhibits VEGF induced angiogenesis. The term anti-VEGF antibody encompasses full length antibodies and antibody fragments such as Fab, Fab', F(ab)$_2$ and F$_v$ provided said fragments show the desired pharmacological activity by binding to human VEGF. Ranibizumab has a binding affinity to VEGF (Kd) of no more than about $1 \times 10^{-8}$ M-i.e., of about $1.4 \times 10^{-10}$) (see Chen et al, on page 870). FIGS. 10A and 10B of the '269 patent provide the sequences of the light chain variable and heavy chain variable domains of ranibizumab (Fab Y0317 as shown in Chen et al.). These sequences are identical to SEQ ID NO: 115 and SEQ ID NO: 116 of the '269 patent.

In addition to ranibizumab and other anti-VEGF inhibitors or drugs described in the above articles and patents, additional anti-VEGF or anti-angiogenic drugs may also be utilized in the present formulation. While the inventors have discovered that anti-VEGF antibodies that are antibody fragments are preferred in the liposomal formulations for the treatment of diseases and conditions that involve topical application to the eyes of patients having, healthy corneas or di minimus neovascularization of the cornea but some other ocular condition (e.g. age related macular degeneration or diabetic macular edema), formulations comprising whole anti-VEGF antibodies and self-forming, thermodynamically stable liposomes are also useful in the treatment of conical neovascularization and these other ocular diseases (in patients having both diseases) provided the corneal neovascularization permits or facilitates the entry of the large whole antibody and formulations thereof. An example of an intact or whole anti-VEGF antibody is sold by Genentech under the brand name AVASTIN® (bevacizumab). This antibody is a recombinant humanized IgG1 antibody that inhibits the biological activity of VEGF. It contains human framework regions and the complementarity-determining regions of a murine antibody that binds to VEGF and has an approximate molecular weight of 149 kD. This antibody is produced in a mammalian cell (Chinese Hamster Ovary) expression system in a nutrient medium containing Gentamycin U.S. Pat. No. 6,054,297 (hereby incorporated by reference in its entirety) claims and discloses bevacizumab or a process for making bevacizumab (see claims 1, 6, 7, 8, 9, 10, 12, 29 and 30 therein).

As described in the approved product package insert, bevacizumab is a recombinant humanized monoclonal IgG1 antibody that binds to and inhibits the biological activity of human vascular endothelial growth factor in in vitro and in vivo assay systems. This antibody contains human framework regions of a murine antibody that binds to VEGF $^6$(see L. G. Presta et al. (1997) Cancer Res. 57: 4593-99). The molecular weight of bevacizumab is about 149 kilodaltons. This paper discloses the interaction of the variable domains of the humanized F(ab) antibody fragment, "F(ab)1-12." Bevacizumab has non-human CDRs derived from the sequence of murine antibody as well as framework substitutions in the variable domains at position 46 in the light chain ($V_L$) and positions 49, 69, 71, 73, 78 and 94 in the heavy chain ($V_H$) that are the same as the substitutions shown at the corresponding: positions of F(ab)-12, as shown in FIG. 1 of Presta et al. Presta et al. has information about the molecular features and binding characteristics of bevacizumab.

Figure 7:
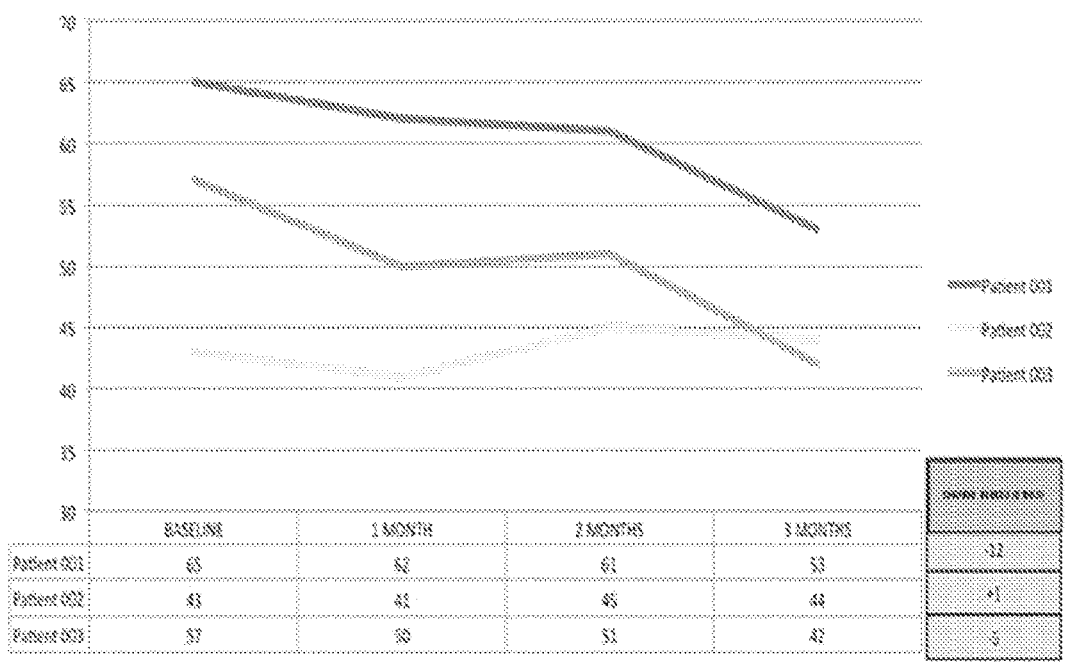
FIG. 7 shows the results of BCVA over time for the contra-lateral eyes.

As stated previously, In addition to ranibizumab and bevacizumab, other known anti-VEGF antibodies or anti-angiogenic drugs may also be utilized in the present invention. The anti-VEGF antibodies of the invention are prepared as described in the patent references cited above with respect to same. In general, isolated nucleic acid encoding the antibody; vectors comprising the nucleic acid are operably linked to control sequences recognized by host cells transformed with the vector; host cells having said vector are all collectively used in a process for producing the antibody of interest after culturing said cells and collecting and purifying the antibody. Any suitable pharmaceutical excipient may be added to the antibody and the antibody may also be lyophilized as desired. The "anti-VEGF antibodies" are inclusive of various forms and may be full length having an intact human Fc region or an antibody fragment-e.g., Fab, Fab' or F(ab')$_2$. The other anti-angiogenic drugs suitable for combining with the lipids disclosed herein to form liposomal formulations include pegaptanib or etanercept (a TNF inhibitor). In the latter case, this formulation may be used to treat various autoimmune diseases or conditions. Etauercept is sold under the trade name Enbrel® which is used to treat rheumatoid, juvenile rheumatoid and psoriatic arthritis, plaque psoriasis and ankylosing spondylitis. Other suitable drugs include sunitinib, a VEGF and PDGF receptor protein kinase and angiogenesis inhibitor (a 2-oxindole sold under the name SUTENT®) and which is described and claimed in U.S. Pat. No. 6,573,293 hereby incorporated by reference) or FOVESTA™ (formerly known as E10030), a regulator of platelet derived growth factor B (PDGF-B)(1.5 mgs/0.5 mgs ranibizumab). Other suitable drugs used in combination include interferon-alpha-2a or temsirolimus or other mTOR inhibitors such as rapamycin. Classes of drugs for ocular diseases that may he used in combination also include proteasomal inhibitors, autophagy inhibitors, retinoids, lysosomal inhibitors, heat shock response activators, Hsp90 chaperone inhibitors, protein transport inhibitors, glycosidase inhibitors, tyrosine kinase inhibitors and histone deacetylase inhibitors. These drugs may be utilized alone in the liposomal formulation or may be used in a combination formulation with an anti-VEGF compound or antibody or may be used in sequential combination and preferably in a topical formulation. The preferred indication when combining FOVISTA™ (0.03-3.0 mgs/eye in combination with 0.5 mg ranibizumab or other anti-VEGF compound)(and/or other drug having PDGF inhibition activity) and ranibizumab is the treatment of age-related macular degeneration. Aflibercept (2.0 mgs/0.05 mL)(Eylea™) may also be used in the liposomal formulation alone or in combination with ranibizumab or other active ingredients. The present invention further includes a topical liposomal formulation as recited herein comprising FOVISTA and aflibercept and/or any other anti-angiogenic drug provided that at least one of the active ingredients is blended/combined with the thermodynamically stable, self forming liposomes of the invention. FOVISTA (an aptamer directed against PDGF-B) is also known and described as "Antagonist A" in U.S. Pat. Pub. No. 2012/0100136 which is hereby incorporated by reference in its entirety. The synthesis of Antagonist A is described in Example 4 in the '136 publication (see also FIG. 7 therein). Each of the individual VEGF antagonists and PDGF antagonists described therein are also included in the scope of the present invention when at least one agent is formulated with a lipid described herein that forms a thermodynamically stable, self forming liposome. A topical formulation having any one of or any combination of the active ingredients recited herein is advantageous over the drugs or combination thereof, that are administered by intravitreal injection. In addition, topical application to the eye for an ocular disease is preferable to systemic oral administration. The compositions useful in the present invention include, as liposomal formulations or liposomal formulations and/or any other formulation in combination, (a) (PDGF inhibitors) ARC-127, Antagonist A, Antagonist B, Antagonist C, Antagonist D, 1B3 antibody, CDP860, IMC-3G3, imatinib, 162.62 antibody, 163.31 antibody, 169.14 antibody, 169.31 antibody, αR1 antibody, 2A1E2 antibody, M4TS.11 antibody, M4TS.22 antibody, A10, brefeldin A, sunitinib, Hyb 120.1.2.1.2 antibody, Hyb 121.6.1.1.1 antibody, Hyb 127.5.7.3.1 antibody, Hyb 127.8.2.2.2 antibody, Hyb 1.6.1 antibody, Hyb 1.11.1 antibody, Hyb 1.17.1 antibody, Hyb 1.18.1 antibody, Hyb 1.19.1 antibody, Hyb 1.23.1 antibody, Hyb 1.24 antibody, Hyb 1.25 antibody, Hyb 1.29 antibody, Hyb 1.33 antibody, Hyb 1.38 antibody, Hyb 1.39 antibody, Hyb 1.40 antibody, Hyb 1.45 antibody, Hyb 1.46 antibody, Hyb 1.48 antibody, Hyb 1.49 antibody, Hyb 1.51 antibody, Hyb 6.4.1 antibody, F3 antibody, Humanized F3 antibody, C1 antibody, Humanized C1 antibody, 6.4 antibody, anti-mPGDF-C goat IgG antibody, C3.1 antibody, 5-methyl-7-diethylamino-s-triazolo (1,5-a) pyrimidine, interferon, protamine, PDGFR-B1 monoclonal antibody, PDGFR-B2 monoclonal antibody, 6D11 monoclonal antibody, S is 1 monoclonal antibody, PR7212 monoclonal antibody, PR292 monoclonal antibody, HYB9610 monoclonoal antibody, HYB 9611 monoclonal antibody, HYB 9612 monoclonal antibody, HYB 9613 monoclonal antibody, 4-(2-(N-(2-carboxamido-indole)aminoethyl)-benzenesulfonate, 4-(2-(N-(-2-carboxamideindole)aminoethyl)-sulfonylurea, CGP 53716, human antibody g162, pyrazolo [3,4-g]quinoxaline, 6-[2-(methylcarbamoyl) phenylsulphanyl]-3-E-[2-(pyridine-2-yl)ethenyl]-indazole, 1-{2-[5-(2-methoxy-ethoxy)-benzoimidazole-1-yl]-quinoline-8-yl}-piperidine-4-ylamine, 4-4-[N-(4-nitrophenyl)carbamoyl]-1-piperazinyl]-6,7-dimethoxyquinazoline, 4-amino-5-fluoro-3-(6-(4-methyl-piperazine-1-yl)-1H-benzimidazole-2-yl)1H-quinoline-2-one, (4-tert-butylphenyl) {4-[(6,7-dimethoxy-4-quinolyl)oxy]phenyl}methancone, 5-methyl-N-[4-(trifluoromethyl)phenyl]-4-izoxazolecarboxamide, trans-4-[(6,7-dimethoxyquinoxaline-2-yl)amino] cyclohexanol, (Z)-3-[(2,4-dimethyl-5-(2-oxo-1,2-dihydroindole-3-ylidenemethyl)-1H-pyrrole-3-yl)-propionic acid, 5-(5-fluoro-2-oxo-1,2-dihydroindole-3-ylidenemethyl)-2,4-dimethyl-1H-pyrrole-3-carboxylic acid, 1-(4-chloroanilino)-4-(4-pyridylmethyl)phthalazine, N-{4-(3-amino-1H-indazole-4-yl)phenyl-N"-(2-fluoro-5-methylphenyl)urea, 1,2-dimethyl-7-(2-thiophene)imidazole[5,4-g]quinoxaline, 1,2-dimethyl-6-phenyl-imidazolo[5,4-g]quinoxaline, 1,2-dimethyl-6-(2-thiophene)imidazolo[5,4-g]quinoxaline, AG1295, AG1296, 3-arylquinoline, 4-pyridyl-2-arylpyrimidine, sorafenib, MLN518, PKC412, AMN107, suramin neomycin or a pharmaceutically acceptable salt thereof and (b) (VEGF inhibitors) ranibizumab, bevacizumab, aflibercept, KH902 VEGF receptor-Fe fusion protein, 2C3 antibody, ORA102, pegaptanib, bevasiranib, blunt ended bevasiranib, SIRNA-027, deeursin, decursinol, picropodophyllin, guggulsterone, PLG101, eicosanoid LXA4, PTK787, pazopanib, axitinib, CDDO-Me, CDDO-Imm, shikonin, betahydroxvisovaleryishikonin, ganglioside GM3, DC101 antibody, Mab 25 antibody, Mab73 antibody, 4A5 antibody, 4E10 antibody, 5F12 antibody, VA01 antibody, BL2 antibody, BECG-related protein, sFLT01, sFLT02, Peptide B3, TG100801, sorafenib, G6-31 antibody or other compounds which inhibit VEGF related angiogenesis. In addition to antibodies, other protein based active ingredients suitable to treat ophthalmic diseases or conditions, including diseases of the front of the eye such as corneal diseases or healing necessary due to surgical incisions; trauma or ulcers, includes, for example, human growth hormones or other known hormonal peptides or variants thereof.

The liposomal formulation is prepared by following the following general steps in any order: (1) provision of an aqueous solution containing an anti-VEGF antibody and/or other active or actives as described above; (2) addition of a thermodynamically stable, self-forming lipid capable of forming a liposome to said aqueous solution of step (1) and (3) optional addition of pharmaceutically acceptable excipients. Any variation of a process to prepare the liposomal suspension formulation may be utilized including combining, the anti-VEGF antibody (or VEGF inhibitor or PDGF inhibitor) and the lipid and then adding an aqueous solution or adding each ingredient separately to an aqueous solution. The suspension is prepared based upon the expected route of delivery (e.g. topical etc.) and the additional excipients are selected based upon such route as well. Carriers, stabilizers and/or excipients include buffers such as phosphate, citrate or other inorganic acids; antioxidants such as ascorbic acid and/or methionine; preservatives; low molecular weight polypeptides; proteins such as gelatin, serum albumin or immunoglobulins; hydrophilic polymers such as PVP; amino acids; monosaccharides or disaccharides or other carbohydrates; chelating agents; sugars; salt forming counter-ions; non-ionic surfactants and the like. The liposomal formulation may also be in the form of a solution.

The formulations are useful in the treatment of VEGF related diseases and disorders. The preferred diseases or conditions to be treated with the formulation described herein are ocular diseases. As described above, the preferred disease or condition for the present invention is the treatment of diabetic macular edema. As referenced above, DME results from a series of biochemical and cellular events that ultimately cause progressive leakage and exudation, leading to thickening of the retina and the formation of hard exudates within one disc diameter of the center of the macula. Laser photocoagulation is the mainstay of treatment and is effective to prevent the risk of moderate visual loss by about 505 [ETDRSRG, 1985]. Laser photocoagulation leads to improvement in reading line scores but has associated complication such as progressive enlargement of scars, central scotomata, decreased contrast sensitivity and impaired color vision.

The liposomal formulation may broadly treat tumors or retinal disorders associated with VEGF and/or PDGF or any other ophthalmic disease or condition depending upon the particular active ingredient. The anti-VEGF antibodies inhibit one or more of the biological activities caused by VEGF. Therapeutic applications involve a pharmaceutically acceptable dosage form administered to a patient in need of treatment of the particular disease or condition. Suitable dosage forms while preferably topical may also include administration by intraveneous means as a bolus or by continuous infusion; intramuscular, intreperitoneal, intracerobrospinal, subcutaneous, intraarticular, intrasynovial, intrethecal, oral or by inhalation. In addition, such antibody formulations may also be administered by intra tumoral, periturnoral, intrelesional or perilesional routes. The neoplastic diseases amenable to treatment with the antibody formulations include various carcinomas including breast carcinoma, lung carcinoma, gastric carcinoma, esophageal, colorectal, liver, ovarian, arrhenoblastomas, cervical, endometrial, endometrial hyperplasia, endometriosis, fibrosacromas, choriocarcinoma, head and neck cancer, nasopharyngeal carcinoma, laryngeal carbinomas, hepatolastoma Kaposi's sarcoma, melanoma, skin carcinomas, hemangioma, cavernous hemangioma, hemangioblastoma, pancreas carcinomas and other types of cancer. Non-neoplastic conditions that are VEGF related include rheumatoid arthritis, posriasis, atherosclerosis, diabetic and other proliferative retinopathies including retinopathy of prematurity, retrolental fibroplasias, neovascular glaucoma, age-related macular degeneration, diabetic macular edema and other forms of macular edema, thyroid hyperplasias including Grave's disease, corneal and other tissue transplantation, chronic inflammation, lung inflammation, nephritic syndrome, preecilampsia, ascites, pericardia effusions and pleural effusion. The preferred condition or disease treated with the preferred topical formulation is diabetic macular edema. The dosage administered and the frequency of administration will depend upon the type and severity of the disease and the particular patient's condition. For example, the anti-VEGF antibodies may be administered at a dosage range of 1 µg/kg to about 50 mg/kg or about 0.1-20 mg/kg to a patient in need of treatment thereof. The preferred dosage regimen for the treatment of DME and with respect to the topical formulation of ranibizumab is described in Example 3 herein. The concentration and amount of active ingredient may be varied depending upon the particular patient and the number of days treated and amount provided per day or week or month may also be varied depending upon the patient's response and signs of improvement in both visual acuity and in retinal thickening.

An ideal treatment modality for purposes of treating DME or other VEGF related ocular condition would be one that leads to rapid and long lasting vision improvement. The other treatment modalities currently used for the treatment of DME include selective PKCβ inhibitors (ruboxistaurin); steroids (triamcinolone acetonide, fluocinolone acetonide); VEGF inhibitors (bevacizumab; ranibizumab and pegaptinib-injectables) and vitrectomy. The present liposomal formulation provides a topical treatment regimen that is a significant improvement over, for example, intravitreal formulations currently on the market. The present formulation can be used in combination with other known treatments for the ocular or VEGF related diseases or conditions recited herein and/or as described above and provided there are no contraindications. Such treatment regimens or therapeutic approaches include, for example, siRNA molecules such as bevasiranib and with appropriate delivery vehicles including the thermodynamically stable, self forming liposomes utilized in the current invention.

Ophthalmic steroids that may be utilized in the liposomal formulation alone or in combination with any other active ingredient include dexamethasone, fluocinolone, loteprednol difluprednate, fluorometholone, prednisolone, medrysone, triamcinolone acetonide, rimexolone and the various salt forms thereof. Other ophthalmic anti-inflammatory agents (for example NSAIDs) may also be utilized in the liposomal formulation. Depending, upon the active ingredient, other liposomes in addition to or as an alternative to the thermodynamically stable self-forming liposomes may be utilized.

The following examples are intended to further illustrate certain embodiments of the invention and are non-limiting:

EXAMPLES

Example 1

A Solution of Liposomes and Ranibizumab

A vial containing 0.5 mg of ranibizumab at a concentration of 10 mg/mL (0.05 mL) was obtained. 0.015 grams of PEG-12 glycerol dimyristate (PEG-12 GDM) Qsomes™ was added to this solution (the number after PEG indicates the number of $C_2H_4O$ subunits in the PEG chain). The volume of this liposomal suspension was diluted to a final volume of 1.5 mL using 1.45 mL of a buffer solution consisting of phosphates, sodium chloride and polioxyl 40 stearate to provide a ranibizumab concentration of 0.333 mg/mL in the liposomal suspension and a lipid percentage of about 1% (10 mg/mL). Sodium perborate (0.28 mg/mL) was added as a preservative. 1 mL of this suspension is equivalent to 20 drops. Each drop contains approximately 17 μg ranibizumab.

Figure 3:
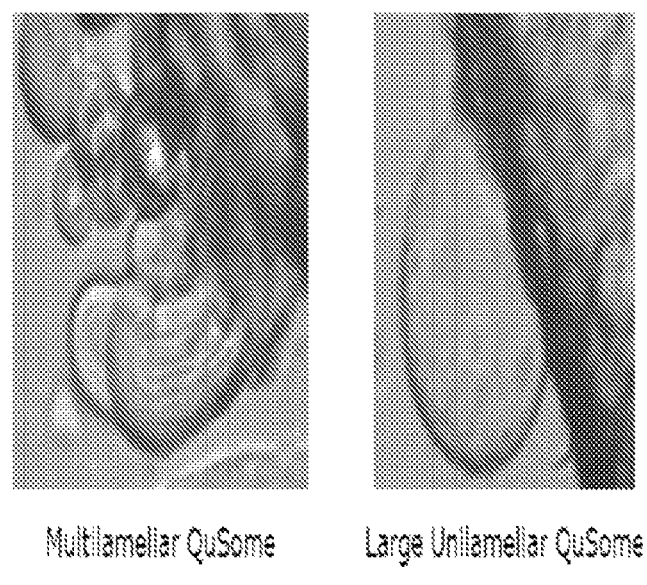
FIG. 3 shows microscopy pictures of multilamellar liposomes and unilamellar liposomes.
Figure 4:
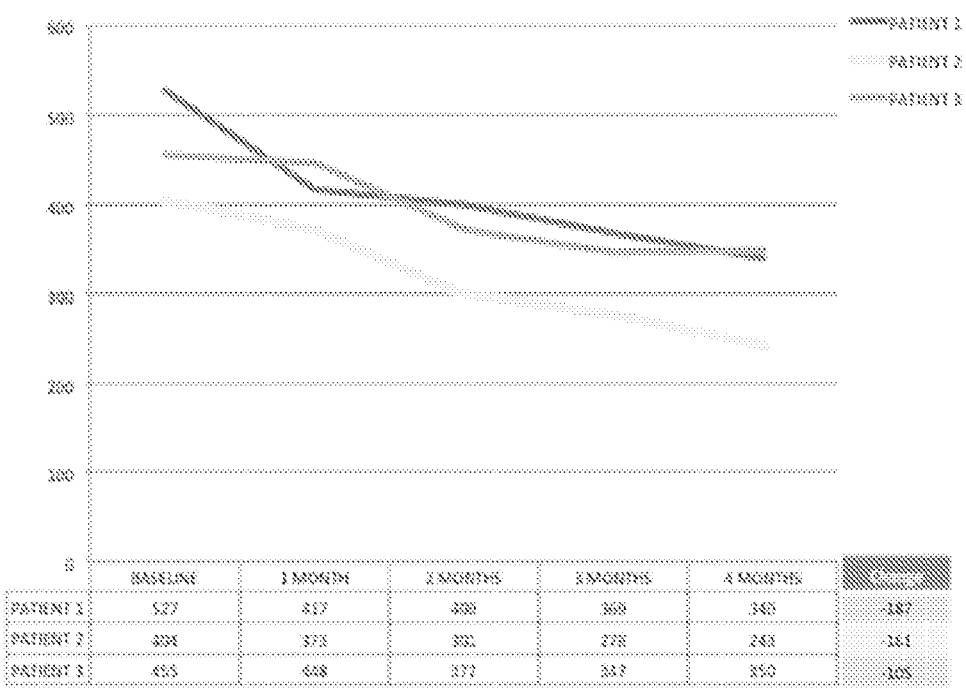
FIG. 4 shows OCT results of Central Foveal thickness of patients treated with the liposomal formulation of ranibizumab over time.
Figure 5:
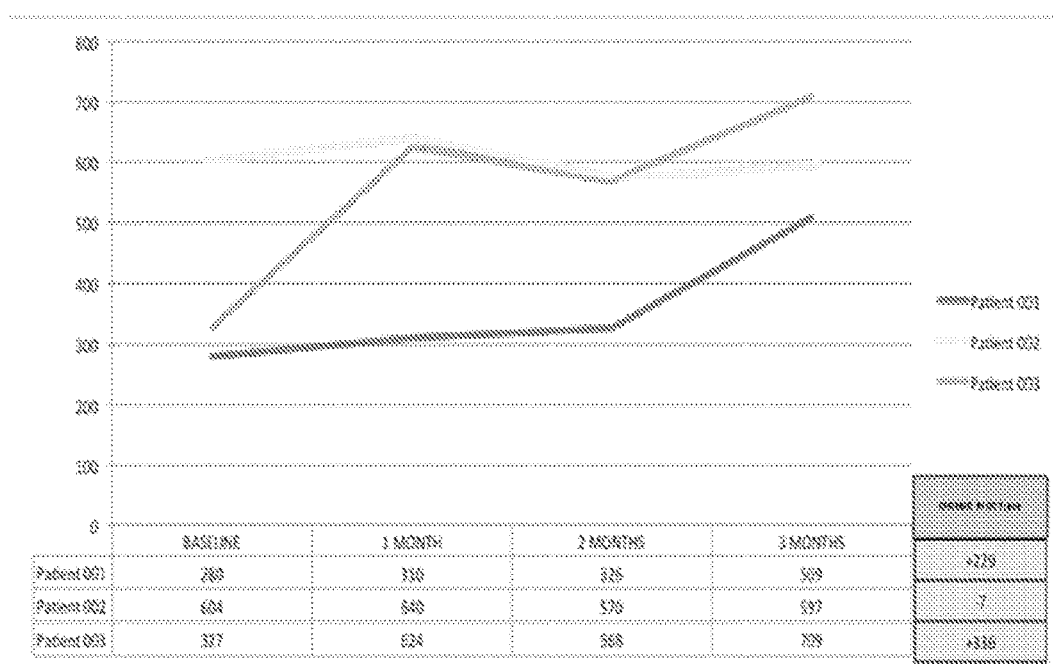
FIG. 5 shows OCT results of Central Foveal thickness of the patients' contra lateral eyes over time.
Figure 6:
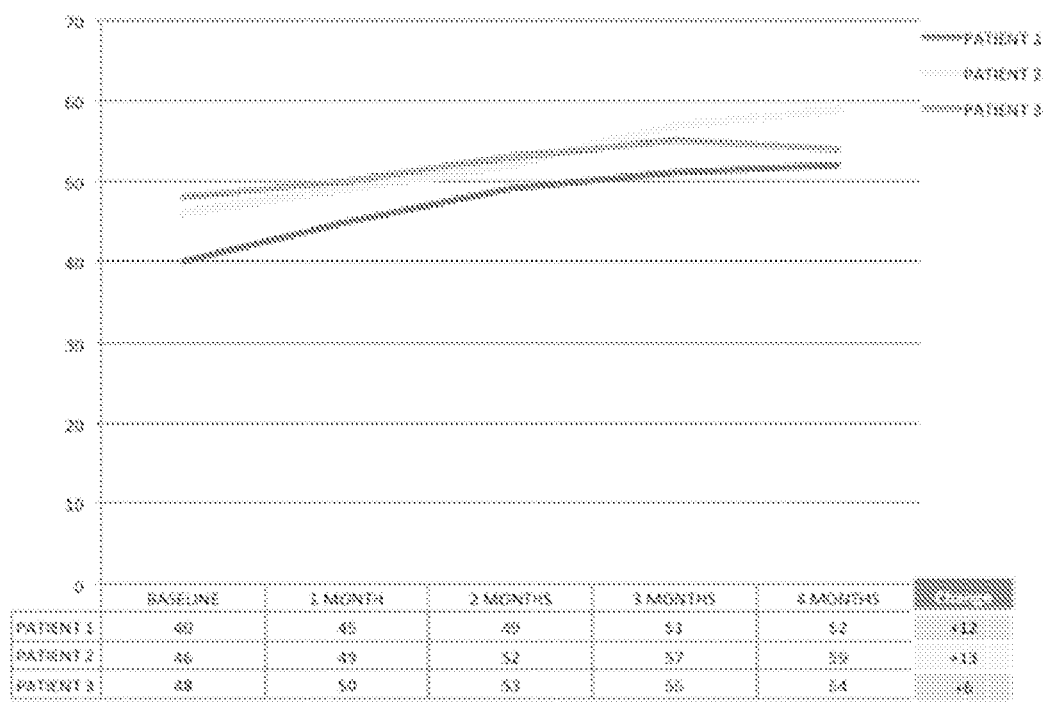
FIG. 6 shows the results of BCVA over time for the study eyes in the three patients.

The buffer solution was prepared by combining a 15 mL solution of polyoxyl 40 stearate, sodium chloride, sodium monobasic phosphate and sodium dibasic phosphate with 5 mLs of the sodium perborate solution (V=20 mL, pH 5.5). 1.45 mLs of this solution was then utilized as described directly above. The concentration of each of the excipients in the ophthalmic liposomal suspension formulation was 0.142 mg/mL (sodium phosphate dibasic); 6.7 mg/mL (sodium phosphate monobasic); 50 mg/mL (polioxil 40 stearate); 5.1 mg/mL (sodium chloride); 0.333 mg/mL (ranibizumab); 10 mgs/mL (PEG-12 GDM) and 2.8 mg/mL (sodium perborate). The pH may be adjusted with HCl or NaOH and low molecular weight amino acids or organic acids may be utilized as well. FIG. 3 shows at least two types of liposomes (Qusomes®) that are formed when the lipid is mixed with an aqueous solution (from Biozone Laboratories website).

Example 2

Diffusion Chamber Study in Rabbit Corneas

Diffusion chamber data of the liposomal formulation applied to rabbit corneas was generated using the methods described below. To summarize, samples were taken at 10, 20 and 30 minutes and at hours 1, 2, 3, 4, 5, 6 and 24. The data showed a significant rate of penetration into the aqueous humor of rabbit corneas at 34 degrees Centigrade for the liposomal ranibizumab formulation applied topically In the liposomal formulation ranibizumab was identified starting at 3 hours and remained present up to 24 hours post administration versus 7 and 14 days previously reported in the rabbit for a non-liposomal formulation (data not shown-see Chen et al., Eye London 2011 November; 25(11):1504-11.). Experiments were conducted in glass, Valia-Chen chambers with horizontal flow. The water recirculates with a temperature of 34 degrees C. A membrane was placed between the junctions of the chambers and, in this example, rabitt corneas were used as the membrane. The receptor chamber was filed with 3.2 mLs of saline solution to simulate the content of aqueous humor in the anterior portion of the eye. The donor chamber was provided with 3 mLs of the ophthalmic formulation comprising ranibizumab and the thermodynamically stable, self-forming lipid. The diffusion chambers were constantly agitated. Samples were collected from the receptor chamber at various timepoints-400 μL samples were taken and replaced with 400 μLs of saline solution each time. The samples were taken at time points: 10 min; 20 min; 30 min; 1 hr; 2 hr; 3 hr; 4 hr; 5 hr; 6 hr and 24 hr. Ranibizumab was detected by HPLC as early as the $3^{rd}$ hour. Lucentis® was used as a control solution for the HPLC standard. Electrophorosis was also used to evaluate the passage of the liposomal formulation through the rabbit cornea membrane and results were consistent with the HPLC data.

Example 3

Pilot Clinical Study on Patients with DME

Figure 2:
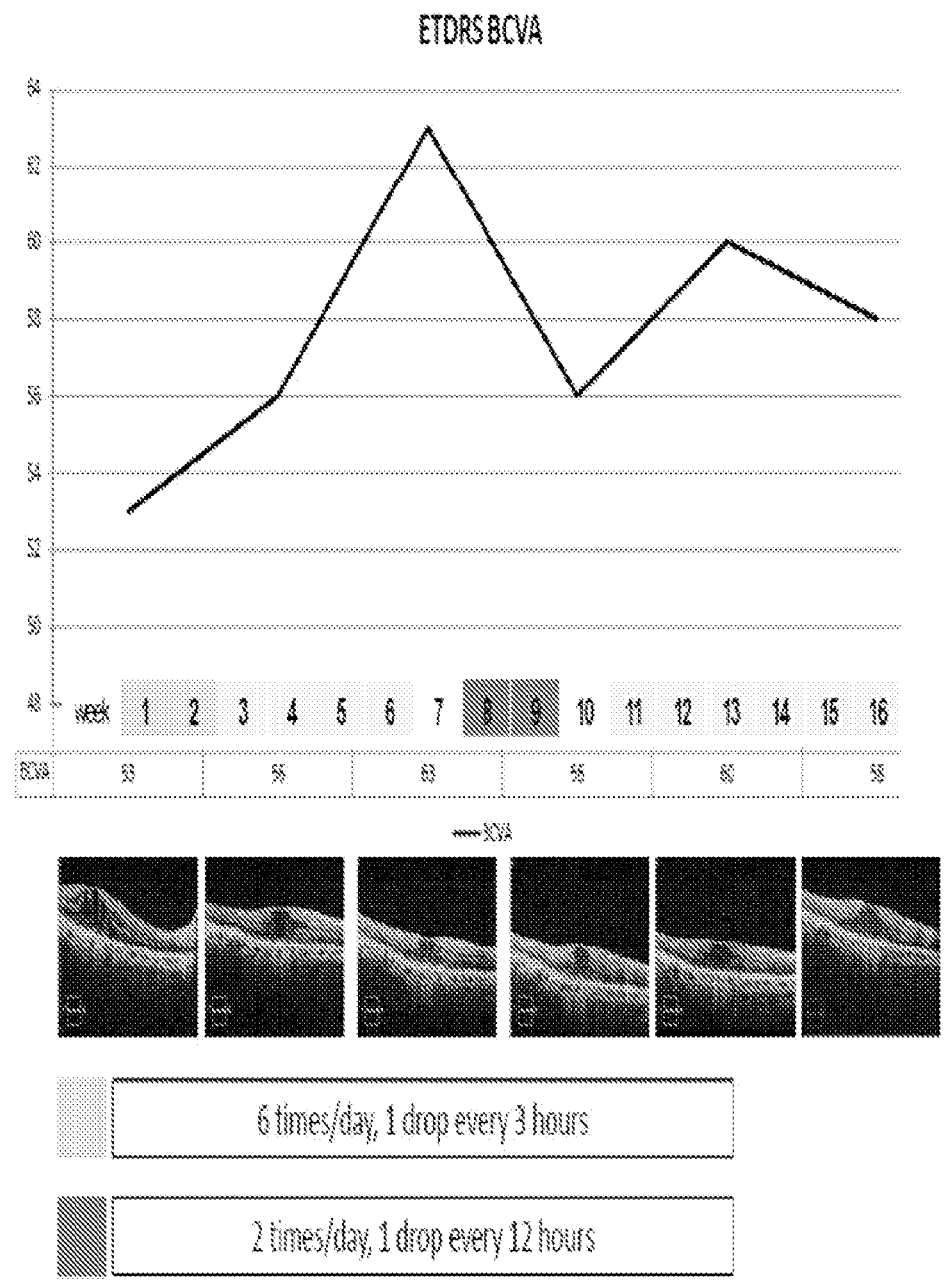
FIG. 2 shows the same clinical patient treated with a liposomal ranibizumab formulation having improved visual acuity measurements (ETDRS BCVA) over an eight week period after being dosed six drops per day for two weeks. At week eight the patient showed a decrease in VA and treatment was reinitiated at 10 weeks at a daily dose of 2 drops per day.

A patient having DME was treated six times/day with 1 drop/every three hours of the formulation on a daily basis (6×/day) for two weeks. The total dose/day of ranibizumab was 6×17 ug or 102 ug. Improvements in loss of mean central foveal thickness (CFT) and an increase in visual acuity were seen through six weeks following this two week period (See FIG. 1 and FIG. 2). At week eight an increase in retina thickness and decline in visual sharpness occurred and, at week 10, treatment was reinitiated at two drops per day (34 ug/day). At week 14 clear tendency toward improvement in OCT and BCVA was observed (see FIGS. 1 and 2). Two additional patients were also treated using the same protocol. Results of all three patients are presented in FIGS. 4-7 and show improvement in CFT and VA relative to control.

Example 4

Pilot Clinical Study on Patients with DME Using Triamcinolone Actetonide

Eligible patients having DME received a topical formulation comprising triamcinolone (TA) in a single center open label pilot study. A total of 3 eyes of 3 patients (mean age 58 years, range 53-64) with DME involving the center of the macula and best-corrected visual acuity (BCVA) in the study eye between 65 and 40 letters using ETDRS testing. Patients were instructed to apply one drop containing 133 ug (micrograms) of TA every two hours in the study eye, while they were awake (six times) during the controlled treatment period of twelve (12) weeks. The main outcome measures included primary end points at three months such as the frequency and severity of ocular and systemic adverse events and the change from baseline in the central foveal thickness (CFT), as measured by optical coherence tomography (OCT) over time. The secondary outcomes were the change from baseline BCVA score over time, proportion of patients with a >3-step progression from baseline in ETDRS retinopathy severity on fundus photographs (FP), proportion of patients with resolution of leakage on fluroescein angiography (FA) and the need of macular laser treatment over time. The TA formulation was prepared in a similar manner to the ranibizumab formulation from commercially available starting materials.

Triamcinolone+1% Liposomes Ophthalmic Suspension
The final formulation is sterile, aqueous suspension. Its content is as follows:

| TA FORMULATION | |
|---|---|
| | mg/mL |
| Triamcinolone acetonide * | 2.667 |
| Hydroxypropylmethylcellulose | 3.000 |
| Mono basic sodium phosphate | 10.000 |
| Dibasic sodium phosphate | 3.000 |
| Polysorbate 80 | 0.500 |
| EDTA | 0.100 |
| Sodium chloride | 2.500 |
| Benzalkonium Chloride 50% | 0.200 |
| PEG-12-GDM | 10.0000 |
| Water | 1 mL |
| NaOH or HCl to adjust pH 5.0-7.5 | Each drop of the suspension contains 133.35 μg. |

PEG-12-GDM: Liposomes; Diacylglycerol-polyethyleneglycol (PEG 12), glycerol dimyristate (GDM).
* TA is a finished product. It is TA micronized (approx. 12 mm) and free of preservatives.

Preparation Protocol of Triamcinolone+1% Liposomes Ophthalmic Suspension

1. Place 40% of the final volume of distilled water in a beaker and heat it to 70 to 80° C.
2. Add the hydroxypropylmethylcellulose and stop mixing until reaching room temperature and it becomes a clear and homogeneous mixture.
3. Autoclave it and once sterile allows it to reach room temperature while stirring.
4. Place in another beaker 40% of the final Volume of distilled water. Add and mix until completely dissolved one by one the following reagents:
   a) Sodium phosphate monobasic
   b) Sodium phosphate dibasic
   c) EDTA
   d) Sodium chloride
   e) Polysorbate 80
5. In 10% of the remaining volume of water, add the benzalkonium chloride at 50% and mix until completely incorporated. Once dissolved, add this new solution to the above solution containing phosphates, EDTA, sodium chloride and Polysorbate 80. To sterilize, filter by 0.22 μm membrane.
6. Mix the sterile solution of hydroxypropylmethylcellulose with the other sterile solution containing the salts and the preservative benzalkonium chloride and mix until getting a clear homogeneous mixture.
7. Add the triamcinolone acetate to the solution with buffers and benzalkonium chloride and stir until completely incorporated.
8. Add the Liposomes to this mix and stir during 15 minutes with a magnetic stirrer to obtain a final suspension.
9. Package the suspension in special eye dropper. Each dropper bottle contained 1.5 mL of this triamcinolone ophthalmic suspension.

Results: The use of a topical formulation comprising TA in the liposomal formulation in patients with center-involving clinically significant DME was well tolerated. Neither ocular nor systemic adverse events were reported. At month 2, the CFT of all three patients was reduced relative to baseline. Two of the three patients had a decrease in CFT of at least 100 um. At month three, all three patients showed visual acuity improvement. One of the patients gained >15 letters.

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize or be able to ascertain using no more than routine experimentation, numerous embodiments of the claimed invention which may not have been expressly described. Such embodiments are within the scope of the invention.

REFERENCES

1. Roskoski Jr. Sunitinib: A VEGF and PDGF receptor protein kinase and angiogenesis inhibitor. BBRC, 2007.
2. Fong D, Diabetic Retinopathy. Diabetes Care, 2004.
3. Bhagat N, Diabetic Macular Edema: Pathogenesis and Treatment. Survey of Ophthalmology 2009.
4. Meyer C, Current Treatment Approaches in Diabetic Macular Edema. Ophthalmologica, 2007.
5. Chen Y, Selection and analysis of an optimized Anti-VEGF antibody Crystal structure of an affinity-matured Fab in complex with antigen, JMB, 1999.
6. Presta L, Humanization of an Anti-vascular endothelial growth factor monoclonal antibody for the therapy of solid tumors and other disorders.
7. ETDRSR, Photocoagulation for macular Edema, Report 1, 1985,

What is claimed is:

1. A topical aqueous ophthalmic formulation for treating a posterior segment disease or condition by topical delivery to the eye comprising a non-ionic surfactant, a pharmaceutically effective amount of a steroid and a thermodynamically stable, self-forming liposome formed from a PEG-based lipid wherein the weight percentage of the lipid in the total weight of the formulation is less than 20% wt/wt wherein the steroid is selected from triamcinolone acetonide; the liposome is selected from the group consisting of a PEG-12 glyceryl dimyristate or a PEG-12 glyceryl dioleate and the pH of the topical aqueous ophthalmic formulation ranges from about 5.0 to 7.5.

2. The formulation according to claim 1 wherein the posterior segment disease or condition is selected from age-related macular degeneration or diabetic retinopathy.

3. A topical ophthalmic formulation comprising a thermodynamically stable self-forming liposome having a polyethylene glycol (PEG) chain and a glycerol backbone, an active ingredient selected from triamcinolone acetonide, a surfactant, and a buffer reagent which maintains the pH at a range of about 5 to 7.5 wherein the glycerol backbone is selected from the group consisting of glycerol dilaurate (GDL), glycerol dioleate (GDO), glycerol dimyristate (GDM), glycerol dipalmitate (GDP) or glycerol distearate (GDS) and the PEG chain is selected from PEG-12 and the buffer reagent is a citrate buffer and the surfactant is a non-ionic surfactant and wherein the liposome is a self-forming thermodynamically stable liposome present in a weight percentage of less than 20% wt/wt based upon the total weight of the formulation.

4. The formulation according to claim 3 wherein the the thermodynamically stable self-forming liposome is selected from PeG-12-GDM, PEG-12-N1-GDO, PEG-12-Ac2-GDO; PEG-12N1-GDM; or PEG-12-Ac2-GDM; wherein N1 is amine; Ac1 is succinyl and Ac2 is acetyl.

5. A method of treating diabetic macular edema in a patient in need of treatment thereof comprising topically administering to the surface of the eye a pharmaceutically effective amount of a topical ophthalmic formulation comprising a thermodynamically stable self-forming liposome selected from the group consisting of PEG-12-GDM or PEG-12 GDO and triamcinolone acetonide wherein the liposome is a self-forming thermodynamically stable liposome present in a weight percentage of less than 20% wt/wt based upon the total weight of the formulation.

6. The method according to claim 5 wherein triamcinolone acetonide is administered at a dosage range of 50-150 µg/per drop of formulation and applied topically one drop to the eye every two hours 4-6×/day.

7. The method according to claim 5 wherein the patients showed an improvement in central foveal thickness and/or visual acuity.

8. A method of treating a patient having diabetic retinopathy or diabetic macular edema comprising administering a liposomal topical ophthalmic formulation comprising a self-forming thermodynamically stable liposome comprising a PEG-based lipid conjugate selected from a diacylglycerol-PEG compound wherein the conjugate has a melting point below about 40 degrees C; an acyl chain of greater than or equal to about 14 carbons in length and the PEG chain has a molecular weight of between about 300-5000 Daltons and an active pharmaceutical agent selected from triamcinolone acetonide wherein said formulation is suitable for topical delivery to the eye of the patient to treat the posterior segment disease or condition without side effects or complications associated with an intravitreal injection wherein the posterior segment disease or condition is selected from diabetic retinopathy or diabetic macular edema and wherein the weight percentage of the self-forming thermodynamically stable liposome (wt/wt) is less than 20% based upon the total weight of the formulation.

9. The method according to claim 8 wherein the side effects or complications are selected from the group consisting of patient discomfort, infectious endophthalmitis, retinal detachment, intraocular pressure changes and traumatic cataract.

10. The method according to claim 8 wherein the ophthalmic formulation further comprises a surfactant and a buffer reagent.

11. The method according to claim 10 wherein the surfactant comprises a non-ionic surfactant triamicinolone acetonide.

12. The method according to claim 11 wherein the corticosteroid is selected from triamcinolone acetonide and the self forming thermodynamically stable liposome comprises PEG-12-glyceryl dimyristate or PEG-12 glyceryl dioleate.

13. The method according to claim 12 wherein the self-forming thermodynamically stable liposome is selected from PEG-12-gylceryl dimyristate.

14. The method according to claim 9 wherein the active ingredient is triamcinolone acetonide; the self-forming thermodynamically stable liposome is PEG-12-GDM and the surfactant is a non-ionic surfactant.

15. The method according to claim 8 wherein the thermodynamically stable self-forming liposome is liquid at 25 degrees C., is self-forming at both 20 degrees C. and at 37 degrees C. and forms when combined with aqueous solution.

16. The method according to claim 8 with the proviso that dexamethasone is excluded.

* * * * *